(12) United States Patent
Leonardi

(10) Patent No.: US 9,414,599 B2
(45) Date of Patent: Aug. 16, 2016

(54) PROCESS FOR THE PREPARATION OF A METAL COMPLEX IN AN OILY ORGANIC MATRIX

(75) Inventor: Giuliano Leonardi, Isola Dovarese (IT)

(73) Assignee: Volare & Connecting, LLC, St. Louis, MO (US)

( * ) Notice: Subject to any disclaimer, the term of this patent is extended or adjusted under 35 U.S.C. 154(b) by 238 days.

(21) Appl. No.: 14/124,222

(22) PCT Filed: Jun. 7, 2012

(86) PCT No.: PCT/IB2012/052871
§ 371 (c)(1),
(2), (4) Date: Dec. 5, 2013

(87) PCT Pub. No.: WO2012/168891
PCT Pub. Date: Dec. 13, 2012

(65) Prior Publication Data
US 2014/0100202 A1    Apr. 10, 2014

(30) Foreign Application Priority Data
Jun. 8, 2011    (IT) .............................. MI2011A1033

(51) Int. Cl.
| | | |
|---|---|---|
| A01N 55/02 | (2006.01) |
| B01J 31/04 | (2006.01) |
| A61K 31/60 | (2006.01) |
| A01N 59/16 | (2006.01) |
| A01N 59/20 | (2006.01) |
| A61K 33/26 | (2006.01) |
| A61K 33/30 | (2006.01) |
| A61K 33/32 | (2006.01) |
| A61K 33/34 | (2006.01) |
| A61K 33/36 | (2006.01) |
| A61K 33/38 | (2006.01) |
| A61K 45/06 | (2006.01) |
| A61K 33/24 | (2006.01) |
| A61K 8/368 | (2006.01) |
| A61Q 5/02 | (2006.01) |
| A61Q 11/00 | (2006.01) |
| A61Q 19/10 | (2006.01) |
| A61K 8/92 | (2006.01) |
| A23L 1/304 | (2006.01) |
| A23K 1/16 | (2006.01) |
| A23K 1/175 | (2006.01) |
| A23K 1/18 | (2006.01) |
| A23L 1/30 | (2006.01) |
| A23D 9/007 | (2006.01) |
| A23K 1/00 | (2006.01) |

(52) U.S. Cl.
CPC ................ *A01N 55/02* (2013.01); *A01N 59/16* (2013.01); *A01N 59/20* (2013.01); *A23D 9/007* (2013.01); *A23K 1/002* (2013.01); *A23K 1/1612* (2013.01); *A23K 1/1751* (2013.01); *A23K 1/1753* (2013.01); *A23K 1/1758* (2013.01); *A23K 1/1813* (2013.01); *A23L 1/30* (2013.01); *A23L 1/304* (2013.01); *A61K 8/368* (2013.01); *A61K 8/922* (2013.01); *A61K 31/60* (2013.01); *A61K 33/24* (2013.01); *A61K 33/26* (2013.01); *A61K 33/30* (2013.01); *A61K 33/32* (2013.01); *A61K 33/34* (2013.01); *A61K 33/36* (2013.01); *A61K 33/38* (2013.01); *A61K 45/06* (2013.01); *A61Q 5/02* (2013.01); *A61Q 11/00* (2013.01); *A61Q 19/10* (2013.01); *B01J 31/04* (2013.01)

(58) Field of Classification Search
CPC ... A23K 1/002; A23K 1/1813; A23K 1/1751; A23K 1/1758; A23K 1/1753; A23K 1/1612; B01J 31/04; A01N 55/02; A61K 8/368; A61K 45/06; A61K 31/60; A61K 33/24
USPC .................. 514/494, 499, 492; 502/170, 171
See application file for complete search history.

(56) References Cited

U.S. PATENT DOCUMENTS

2006/0019852 A1    1/2006    Beers et al.

FOREIGN PATENT DOCUMENTS

| EP | 1878716 A1 | 1/2008 |
|---|---|---|
| WO | 02/29140 A1 | 4/2002 |
| WO | 2008/043396 A1 | 4/2008 |

OTHER PUBLICATIONS

International Search Report and Written Opinion for PCT/IB2012/052871, filed Jun. 7, 2012 (mailed Oct. 16, 2012).

*Primary Examiner* — Porfirio Nazario Gonzalez
(74) *Attorney, Agent, or Firm* — LeClairRyan, a Professional Corporation

(57) ABSTRACT

A process is described for the preparation of a composition comprising a metal complex in an oily organic matrix, the latter being at the same time able to promote the formation of the complex. Said process also envisages that the complex, once formed, is not separated from said oily organic matrix, but the resulting composition is used as such, as having observed that the performances of the complex present therein is thus improved.

9 Claims, No Drawings

PROCESS FOR THE PREPARATION OF A METAL COMPLEX IN AN OILY ORGANIC MATRIX

This application is a national stage application under 35 U.S.C. §371 of PCT Application No. PCT/IB2012/052871, filed Jun. 7, 2012, which claims the priority benefit of Italian Patent Application No. MI2011A001033, filed Jun. 8, 2011.

FIELD OF THE INVENTION

The present invention relates to a process for the preparation of a composition comprising a metal complex in an oily organic matrix, the latter being simultaneously able to promote the formation of the complex. Said process also envisages that the complex, once formed, is not separated from said oily organic matrix, but the resulting composition is used as such, as having observed that in this way the performances of the complex present therein are improved.

BACKGROUND OF THE INVENTION

The kinetics of the formation reaction of a metal process depends on various factors. On an industrial level, for reasons of costs and concentrations, a direct reaction is performed, where possible, between a metal oxide (MO) or metal hydroxide (MOH) and an organic acid (HA) in aqueous solution. The reaction is typically a reversible equilibrium reaction, e.g. as follows:

$$MO + 2HA \rightleftarrows MA_2 + H_2O$$

The presence of water and the pH considerably affect the reaction rate and the equilibrium point.

It is evident that, since water is one of the reaction products, water itself, as solvent, induces the hydrolysis process of the complex, thus shifting left the reaction.

In addition, certain complexing agents as well as certain metals, can be subjected, in their application, to physicochemical attacks of various nature that reduce their effectiveness, even to a complete ineffectiveness. Among many possible examples of such interactions, the following can be mentioned:
  oxidation by simple exposure to the air;
  acid or base or enzymatic hydrolysis during the steps of the preparation of a food, of a supplement, or during the intake thereof (mastication, gastric digestion . . . );
  reaction with other components of the diet (chelation and insolubilisation of the metals by the phytic acid contained in the grains and derivatives).

In turn, the metal chelates are not inert molecules. The metals for example are able to induce oxidations and rancidity, in particular as relates to the double bonds typically present in vegetable oils that are often valuable from a nutritional point of view (such as Ω3 and Ω6, DHA, EPA).

The complexing agents can also have contraindications, due to their chemical characteristics. A typical example is the gastric toxicity of the salicylic acid and salicylates in general due to their interaction with the gastric mucosae.

The object of the present invention is thus to obtain metal complexes capable of overcoming the aforementioned drawbacks.

SUMMARY OF THE INVENTION

The above mentioned object has been achieved through a process for the preparation of a composition comprising a metal complex in an oily organic matrix, comprising the step of reacting a metal oxide, metal hydroxide, metal carbonate or a mixture thereof with a complexing agent in an oily organic matrix, wherein said complexing agent is salicylic acid, ascorbic acid, an aminoacid, monomer of lignin, a C6-C15 aromatic acid, a C6-C15 heteroaromatic acid, nicotinic acid, nicotinamide, rosmarinic acid, sulphanilic acid or a mixture thereof, and said oily organic matrix is vegetable oil, olein, C3-C36 fatty acid, mono-, di- or triglyceride of C3-C36 fatty acid, natural or synthetic wax, spermaceti, lanolin, paraffin, drying oil or a mixture thereof.

For the purposes of the present invention, by the term "metal complex" it is meant a neutral compound having the formula $M_xA_y$, where M is metal, A the complexing agent, x is an integer from 1 to 3 and y is an integer from 1 to 6.

In another aspect, the present invention relates to a composition obtainable by said process, wherein at least 95% by weight, preferably at least 98% by weight, is a mixture of metal complex and oily organic matrix.

In a further aspect, the present invention relates to the use of said composition, in particular as analgesic, anti-inflammatory, antibacterial, anti-diarrhoeal, disinfectant, cicatrisant or anti-seborrhoeic; or as catalyst of reactions in homogenous phase; or as anti-mould or anti-woodworm.

The characteristics and advantages of the present invention will be evident from the following detailed description and from the working examples provided for illustrative and non-limiting purposes.

DETAILED DESCRIPTION OF THE INVENTION

The subject of the present invention is therefore a process for the preparation of a composition comprising a metal complex in an oily organic matrix, comprising the step of reacting a metal oxide, metal hydroxide, metal carbonate or a mixture thereof with a complexing agent in an oily organic matrix, wherein said complexing agent is salicylic acid, ascorbic acid, an aminoacid, monomer of lignin, a C6-C15 aromatic acid, a C6-C15 heteroaromatic acid, nicotinic acid, nicotinamide, rosmarinic acid, sulphanilic acid or a mixture thereof, and said oily organic matrix is vegetable oil, olein, C3-C36 fatty acid, mono-, di- or triglyceride of C3-C36 fatty acid, natural or synthetic wax, spermaceti, lanolin, paraffin, drying oil or a mixture thereof.

In fact, it has been surprisingly observed that the oily matrix promotes the formation of the metal complex $M_xA_y$, since the water that forms is immiscible in the oily matrix and thus spontaneously separates, removing itself from the equilibrium and thus shifting the reaction to the right, i.e. promoting the formation of the metal complex $M_yA_y$.

According to a preferred embodiment, the metal complex has the formula $MA_2$.

Advantageously, the process for the preparation of the composition of the invention takes place in a single step, at the end of which the composition comprising a metal complex in an oily organic matrix is ready for use. No separation of the metal complex from the reaction environment is in fact needed, nor is a distillation or drying of the resulting mixture, in that, as previously explained, initially the oily organic matrix acts as a reaction solvent and then, once the metal complex $M_yA_y$ has formed, the oily organic matrix becomes, together with the latter, an integral part of the final composition. Therefore, in a single step and in a single reaction environment, from a reaction solvent, the oily organic matrix becomes an ingredient of the composition.

Therefore, preferably the process for the preparation of a composition of a metal complex in an oily organic matrix, consists of the step of the reacting a metal oxide, metal hydroxide, metal carbonate or a mixture thereof with a complexing agent in an oily organic matrix, wherein said complexing agent is salicylic acid, ascorbic acid, an aminoacid, monomer of lignin, a C6-C15 aromatic acid, a C6-C15 heteroaromatic acid, nicotinic acid, nicotinamide, rosmarinic acid, sulphanilic acid or a mixture thereof, and said oily organic matrix is vegetable oil, olein, C3-C36 fatty acid, mono-, di- or triglyceride of C3-C36 fatty acid, natural or synthetic wax, spermaceti, lanolin, paraffin, drying oil or a mixture thereof.

In fact, the metal complex that forms within the oily organic matrix is protected against external agents and can therefore express its efficacy in a remarkably superior way, as the oily organic matrix protects the metal complex from air, humidity, acids, bases and enzymes. This means that the storage of the metal complexes is also advantageously easier and more prolonged.

Furthermore, in the case of food use, the delivery of the metal complex takes place only at intestinal level following the action of the lipase on the fatty matrix, thus obtaining the maximum bioavailability of the complex itself in proximity of the intestinal absorption areas.

Preferably, said complexing agent is salicylic acid, thiosalicylic acid, ascorbic acid, alanine, phenylalanine, glycine, isoleucine, leucine, methionine, proline, valine, tryptophan, tyrosine, glycolic acid, lactic acid, malic acid, tartaric acid, citric acid, mandelic acid, 2-hydroxy-4-methylthio butanoic acid, sinapyl alcohol, cumarilic alcohol, coniferyl alcohol, sinapyl acid, cumarilic acid, coniferyl acid, cinnamic acid, ferulic acid, benzoic acid, benzenesulphonic acid, naphthalenesulphonic acid, dipicolinic acid, phenylacetic acid, 1-naphthylacetic acid, nicotinic acid, nicotinamide, rosmarinic acid, sulphanilic acid or a mixture thereof.

More preferably, said complexing agent is salicylic acid, ascorbic acid, glycine, 2-hydroxy-4-methylthio butanoic acid (methionine hydroxy analogue), phenylacetic acid or a mixture thereof.

Preferably, said oily organic matrix is rapeseed oil, soybean oil, seed oil, olive oil, wheat germ oil, palm oil, coconut oil, sesame oil, peanut oil, cottonseed oil, olein, C3-C36 fatty acid, mono-, di- or triglyceride of C3-C36 fatty acid, animal, vegetable, mineral, petroleum or synthetic wax, spermaceti, lanolin, paraffin, hydrogenated oils or fats, tea tree oil (melaleuca oil) or siccative oil such as linseed oil, walnut oil, poppy oil or a mixture thereof.

C3-C36 fatty acids comprise saturated fatty acids, mono-unsaturated fatty acids and poly-unsaturated fatty acids, such as propanoic acid, butanoic acid, pentanoic acid, hexanoic acid, heptanoic acid, octanoic acid, nonanoic acid, decanoic acid, undecanoic acid, dodecanoic acid, tridecanoic acid, tetradecanoic acid, pentadecanoic acid, hexadecanoic acid, heptadecanoic acid, octadecanoic acid, nonadecanoic acid, eicosanoic acid, docosanoic acid, tetracosanoic acid, hexacosanoic acid, octasosanoic acid, triacontanoic acid, dotriacontanoic acid, cis-7-hexadecenoic acid, cis-9-octadecenoic acid, trans-9-octadecenoic acid, cis-11-octadecenoic acid, cis-9-eicosenoic acid, cis-11-docosenoic acid, cis-13-docosenoic acid, cis-15-tetracosenoic acid, 9,12-octadecadienoic acid, 9,11-octadecadienoic acid, 9,12,15-octadecatrienoic acid, 6,9,12,15-octadecatetraenoic acid, 5,8,11,14-eicosatetraenoic acid, 5,8,11,14,17-eicosapentaenoic acid, 7,10,13,16,19-docosapentaenoic acid and 4,7,10,13,16,19-docosahexaenoic acid. More preferably, said oily organic matrix is siccative oil, coconut oil, palm oil, lanolin, wax or a mixture thereof.

Preferably, said metal oxide, hydroxide or carbonate is an oxide, hydroxide or carbonate of Li, Na, K, Mg, Ca, Al, Sn, Pb, Bi, As, Se, TI, V, Cr, Mn, Fe, Co, Ni, Cu, Zn, Mo, Ru, Rh, Pd, Ag, Cd, Pt, Au, Hg, or a mixture thereof.

More preferably, said metal oxide, hydroxide or carbonate is an oxide, hydroxide or carbonate of Li, Mg, Ca, Al, Bi, Se, Mn, Fe, Cu, Zn or a mixture thereof.

According to a preferred embodiment, the process of the invention further comprises a subsequent step of the formation of unit doses, in order to make the resulting composition easier to handle and transport, as well as industrially more manageable. In particular, said unit doses are pearls, flakes, capsules, suppositories, ingots, pellets, granules or tablets.

The reaction is preferably carried out so that the oily fatty organic matrix is in molten state, therefore the reaction is carried out at a reaction temperature of 20° C. to 250° C., preferably 40° C. to 100° C.

In another aspect, the present invention relates to a composition obtainable by said process. In particular, the composition of the invention consists essentially of at least 95% by weight of a mixture of a metal complex $M_yA_y$, and oily organic matrix, the remaining being non-reacted metal oxide, hydroxide or carbonate and/or complexing agent, reaction by-products and traces of water. Preferably, in said composition, at least 98% by weight is a mixture of metal complex and oily organic matrix.

In fact, the oily organic matrix first acts as reaction solvent in the abovementioned process and then is itself an ingredient of the composition of the invention, together with the metal complex.

It should to be understood that all the aspects identified as preferred and advantageous for the preparation process are to be also, analogously, deemed preferred and advantageous for the composition of the present invention.

In a further aspect, the present invention relates to the use of the composition of the invention as an analgesic, anti-inflammatory, antibacterial, anti-diarrhoeal, antimycotic, disinfectant, cicatrisant or anti-seborrhoeic agent. In fact, the metal complexes, suitably preserved and carried by the oily organic matrix, can be used for the aforementioned uses, thus overcoming the drawbacks associated thereto in the prior art.

Particularly suitable for such uses are:
  Zn ascorbate or Zn salicylate, as antibacterial;
  Bi salicylate or Al salicylate, as anti-diarrhoeal;
  Mg salicylate or Cu salicylate, as analgesic and anti-inflammatory; and
  salicylates in neem oil and lanolin, as disinfectant in post dipping treatment in the bovine or ovine breeding.
  Cu and rosmarinic acid in melaleuca oil (tea tree oil) as fungicide in agriculture.

The composition of the invention is also suitable for use as catalyst of reactions in homogeneous phase, or as anti-mould (in particular Zn salicylate) or as anti-woodworm (in particular Zn salicylates, Cu salicylates of Bi salicylate, in linseed oil).

It has in fact been surprisingly observed that the abovementioned uses are particularly advantageous in view of the capacity of the oily organic matrices to solubilise the specific metal complexes and at the same time deliver them to targets.

More detailed examples of such uses are:
  treatments on wooden products with linseed oil or drying oils in general capable of delivering Zn, Cu, Bi and Al complexes;
  impregnation treatment in general for inhibiting biotic attacks (fungi, moulds, bacteria, insects, . . . );
  formulation of functional food additives (anti-diarrhoeals, anti-inflammatories, . . . both for human and animal use);

preparation of creams, salves and ointments;
preparation of additives for toothpastes;
preparation of soaps, shampoos and antibacterial detergents in general;
preparation of creams for leather and hide products to prevent the formation of moulds and therefore adjuvants in the tannery.

Working examples of the present invention are provided for illustrative purposes.

Example 1

Preparation of Zn Salicylates in Linseed Oil 5,392 g (0.039 moles) of salicylic acid were dissolved in 300 ml of linseed oil (under stirring at 50° C. for one hour). Subsequently, 2 g of $Zn(OH)_2$ (0.02 mol) were added and the reaction mixture was brought to 60-65° C. under stirring. At the end of the reaction, the formation of a clear yellow-orange coloured solution was observed. As per the analyses carried out, both by FTIR and NMR, it was found that anhydrous zinc salicylate in linseed oil was formed:

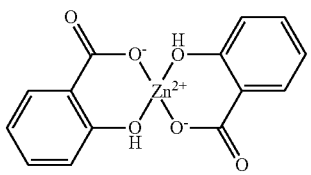

Example 2

Efficacy Test of the Composition of the Invention in the Treatment of Wood

The composition obtained in Example 1 was used to impregnate 10 pieces of pine wood having dimensions of 40×30×3 mm by dipping for 8 hours in order to verify the efficacy against termites (*Kalotermes flavicollis* and *Reticulitermes lucifugus*).

The composition obtained in Example 1 was also tested for efficacy against fungi (white rot and brown rot in wood) in 10 samples of Scots pine by brushing the surface of samples having dimensions of 30×10×5 mm.

It was observed that the wood treated with the composition of the invention offered excellent results in terms of resistance to parasites and also showed excellent resistance properties against the attack by xylophages fungi.

Example 3

Preparation of Cu Salicylate in Hydrogenated Palm Oil 50 kg of hydrogenated palm oil (melting point 60° C.) were melted and added to 15 kg of salicylic acid (108 moles) and 4,300 kg of copper oxide (II) (54 moles). The reaction mixture was maintained at a temperature of 70-90° C. for about one hour until a uniform olive-green coloured composition was obtained. As per the analyses carried out, both by FTIR and NMR, it was found that anhydrous copper salicylate in palm oil was formed:

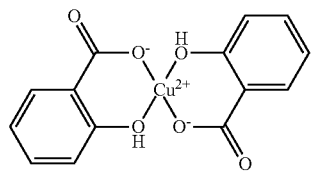

Example 4

Efficacy Test of the Composition of the Invention as Food Additive for Bovines for Anti-Inflammatory Purposes The composition obtained in Example 3 were granulated directly by Spray Cooling. The resulting granules were inserted into known mixtures of mineral-vitamin supplements.

Aim of the Test

During the warmest periods of the year, the farming of beef cattle is subject to various difficulties of a sanitary, zootechnical and operational nature. In the early summer, the persistent high temperatures lead to a progressive drop in food intake on the part of the animals and to a simultaneous increase in water intake. This situation leads to a rapid deterioration of the animal litters, with immediate negative impact on animal wellbeing.

As a consequence of these facts, there is a drastic drop, not only in the daily weight gain, but a drop in the conversions, and an increase in weight-related conditions and sometimes in respiratory conditions. The aim of the test was thus to demonstrate that the administration of the composition of the invention, compared to the usual copper sulphate supplementation, allowed normal food intake to be maintained despite the increase in the external temperature, thus promoting growth and preventing diffused inflammatory conditions.

Test

Two rows of Limousin calves, for a total of 16 boxes, were selected on the basis of genetic homogeneity, live weight and health status: 8 boxes of average weight of 420.80 kg for a total of 64 animals, with 4 being arranged on the west side of the cattle shed and 4 on the east side of the cattle shed.

4 boxes were weighed on the west side and 4 on the east side and were consecutively numbered starting from the west side and the daily consumption of food was quantified with the aid of an optical reader placed on the diet feeder and capable of recording the amount of food administered per box.

Having acknowledged the uniformity of the boxes, from a generic, numeric and average weight standpoint, it was clear that the increase in the average weekly environmental temperature influenced the intake of dry matter by the animals.

The boxes treated with granules of the composition of Example 3 maintained in general a normal intake irrespective of the environmental temperature, thus increasing their intake only in relation to the increase in live weight.

It was therefore surprisingly observed that intake of the composition of the invention improved animal wellbeing, while limiting the negative effect of heat stress and promoting the normal intake of dry matter.

The advantages achieved by means of the process and the composition of the present invention are clear from the detailed description and from the above examples. In particular, said process has proved to be surprisingly and advantageously rapid and convenient, in that it allows the obtainment in a single step of a ready to use composition, wherein the metal complex is long-lasting and retains a high activity and bioavailability over time.

The invention claimed is:

1. Process for preparing a composition comprising a metal complex in an oily organic matrix, said process comprising the step of reacting a metal oxide, metal hydroxide, metal carbonate or a mixture thereof with a complexing agent in an oily organic matrix, wherein said metal oxide, hydroxide, or carbonate is an oxide, hydroxide, or carbonate of Li, Na, K, Mg, Ca, Al, Sn, Pb, Bi, As, Se, TI, V, Cr, Mn, Fe, Co, Ni, Cu, Zn, Mo, Ru, Rh, Pd, Ag, Cd, Pt, Au, or Hg, said complexing agent is salicylic acid, ascorbic acid, an amino acid, lactic acid, malic acid, tartaric acid, citric acid, mandelic acid, 2-hydroxy-4-methylthio butanoic acid (methionine hydroxy analogue), a monomer of lignin, a polymer of lignin, a C6-C15 aromatic acid, a C6-C15 heteroaromatic acid, nicotinic acid, nicotinamide, rosmarinic acid, sulfanilic acid, or a mixture thereof, and said oily organic matrix is vegetable oil, olein, C3-C36 fatty acid, mono-, di- or triglycerides of C3-C36 fatty acid, natural or synthetic wax, spermaceti, lanolin, paraffin wax, siccative oil or a mixture thereof.

2. The process of claim 1, wherein said complexing agent is salicylic acid, thiosalicylic acid, ascorbic acid, alanine, phenylalanine, glycine, isoleucine, leucine, methionine, proline, valine, tryptophan, tyrosine, glycolic acid, lactic acid, malic acid, tartaric acid, citric acid, mandelic acid, 2-hydroxy-4-methylthio butanoic acid (methionine hydroxy analogue), sinapyl alcohol, cumarilic alcohol, coniferyl alcohol, sinapyl acid, cumarilic acid, coniferyl acid, cinnamic acid, ferulic acid, benzoic acid, benzenesulfonic acid, naphthalenesulfonic acid, dipicolinic acid, phenylacetic acid, 1-naphthylacetic acid, nicotinic acid, nicotinamide, rosmarinic acid, sulphanilic acid or a mixture thereof.

3. The process of claim 1, wherein said oily organic matrix is rapeseed oil, soybean oil, seed oil, olive oil, wheat germ oil, palm oil, coconut oil, sesame oil, peanut oil, cottonseed oil, olein, C3-C36 fatty acid, mono-, di- or triglyceride of C3-C36 fatty acid, animal, vegetable, mineral, petroleum or synthetic wax, spermaceti, lanolin, paraffin, hydrogenated fats or oils, tea tree oil (melaleuca oil), or a siccative oil, or a mixture thereof.

4. The process of claim 1, further comprising a subsequent step of formation of unit doses.

5. The process of claim 4, wherein said unit doses are pearls, flakes, capsules, suppositories, ingots, pellets, granules or tablets.

6. Composition obtainable by the process of claim 1, wherein at least 95% by weight is a mixture of the metal complex and the oily organic matrix.

7. An analgesic, anti-inflammatory, antibacterial, anti-diarrhoeal, disinfectant, cicatrisant or anti-seborrhoeic formulation comprising the composition of claim 6.

8. A catalyst for chemical reactions in homogeneous phase comprising the composition of claim 6.

9. An anti-mould or anti-woodworm formulation comprising the composition of claim 6.

* * * * *